United States Patent
Crane et al.

(10) Patent No.: US 10,265,465 B2
(45) Date of Patent: *Apr. 23, 2019

(54) BELT CLIP

(71) Applicant: MEDTRONIC MINIMED, INC., Northridge, CA (US)

(72) Inventors: Chad A. Crane, Granada Hills, CA (US); Jason A. Belton, Norton, OH (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/867,220

(22) Filed: Jan. 10, 2018

(65) Prior Publication Data
US 2018/0126070 A1 May 10, 2018

Related U.S. Application Data

(63) Continuation of application No. 14/636,072, filed on Mar. 2, 2015, now Pat. No. 9,872,954.

(51) Int. Cl.
  *A45F 5/02* (2006.01)
  *A61M 5/142* (2006.01)
  *A61M 25/02* (2006.01)

(52) U.S. Cl.
  CPC ......... *A61M 5/14244* (2013.01); *A45F 5/021* (2013.01); *A61M 25/02* (2013.01); *A45F 2005/027* (2013.01); *A61M 2025/024* (2013.01); *A61M 2025/0206* (2013.01)

(58) Field of Classification Search
  CPC ............... A45F 5/021; A45F 2005/027; Y10T 24/1391; A61M 5/14244

USPC ........................... 224/666, 669, 670; 24/3.11
See application file for complete search history.

(56) References Cited

U.S. PATENT DOCUMENTS

| | | | |
|---|---|---|---|
| 3,907,182 A * | 9/1975 | Bryant | F16B 2/185 224/670 |
| 4,755,173 A | 7/1988 | Konopka et al. | |
| 4,887,753 A * | 12/1989 | Allen | B60R 11/02 224/312 |
| 5,385,282 A * | 1/1995 | Chen | A45F 5/02 224/269 |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,678,281 A * | 10/1997 | Kamp | A45F 5/02 24/3.11 |
| 5,778,497 A * | 7/1998 | Noda | A41F 3/02 24/499 |

(Continued)

*Primary Examiner* — Justin Larson
(74) *Attorney, Agent, or Firm* — Medtronic MiniMed, Inc.

(57) ABSTRACT

A belt clip assembly is disclosed. The belt clip assembly includes a device retainer having a first retainer defined to retain a clip pin. The belt clip assembly further includes a clip coupled to the device retainer via the clip pin and the clip includes a detent and the clip is further defined to retain a tab pin. A tab is coupled to the clip via the tab pin, the tab being rotatable about the tab pin. Wherein the device retainer is initially rotatable about the clip pin independent of rotation of the tab about the tab pin. Additionally, the rotation of the device retainer about the clip pin results in a finite displacement of the device retainer.

14 Claims, 6 Drawing Sheets

(56) References Cited

U.S. PATENT DOCUMENTS

| | | | |
|---|---|---|---|
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,029,871 | A * | 2/2000 | Park ................ A45F 5/02 224/197 |
| 6,101,689 | A * | 8/2000 | Jo ..................... A45F 5/02 24/332 |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,263,702 | B1 * | 7/2001 | Lo ................... A41F 11/06 24/516 |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,110,802 | B1 * | 9/2006 | Kim ................. H04B 1/3888 224/269 |
| 7,131,214 | B1 * | 11/2006 | Blackman ........... A45F 5/02 33/761 |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,070,026 | B2 * | 12/2011 | Wadsworth ......... A45C 11/00 224/197 |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,156,616 | B2 * | 4/2012 | Lo ..................... A45F 5/02 24/3.11 |
| 8,166,615 | B2 * | 5/2012 | Coldiron .......... A44B 15/005 24/3.11 |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,205,776 | B2 * | 6/2012 | Gandhi ............. A45F 5/021 224/666 |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 8,595,903 | B2 * | 12/2013 | Miltner .............. A45F 5/02 24/3.11 |
| 8,806,726 | B1 * | 8/2014 | Lo ..................... A45F 5/02 24/3.12 |
| 2003/0106917 | A1 * | 6/2003 | Shetler ............... A45F 5/02 224/197 |
| 2003/0110595 | A1 * | 6/2003 | Collins .............. A45F 5/02 24/3.12 |
| 2003/0212379 | A1 * | 11/2003 | Bylund ........... A61B 5/14514 604/504 |
| 2005/0116003 | A1 * | 6/2005 | Butler .............. A45C 11/22 224/604 |
| 2006/0084924 | A1 * | 4/2006 | Koch .................. A45F 3/14 604/179 |
| 2007/0123819 | A1 | 5/2007 | Mernoe et al. |
| 2010/0160861 | A1 | 6/2010 | Causey, III et al. |
| 2013/0126565 | A1 * | 5/2013 | Rostami ............ A45F 5/021 224/191 |

\* cited by examiner

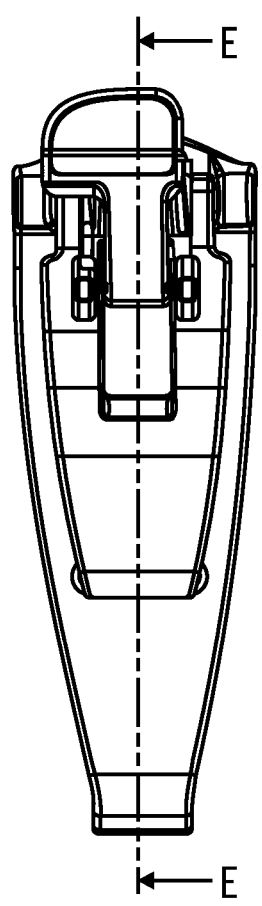 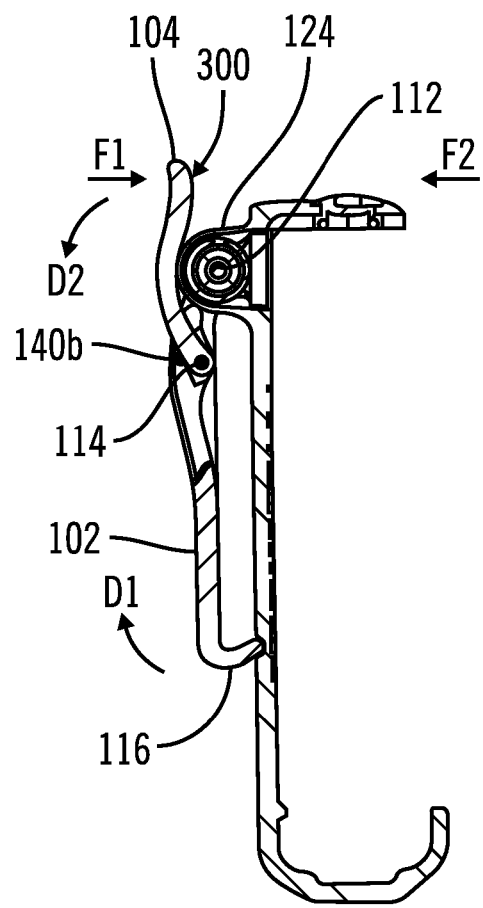
FIG. 3A
SECTION E-E
FIG. 3B

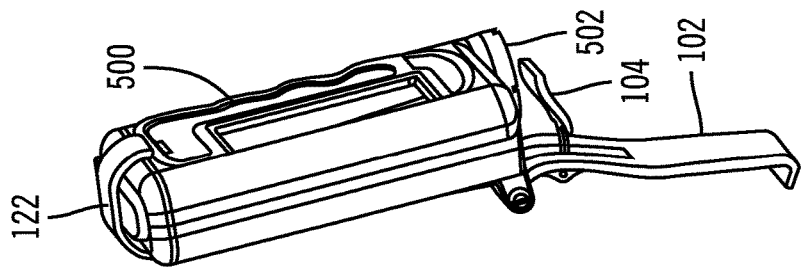
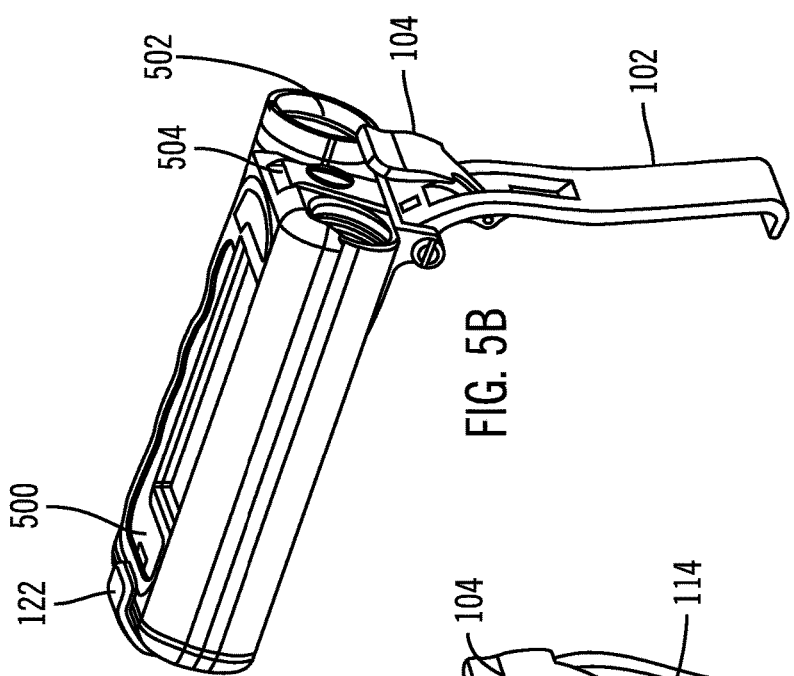
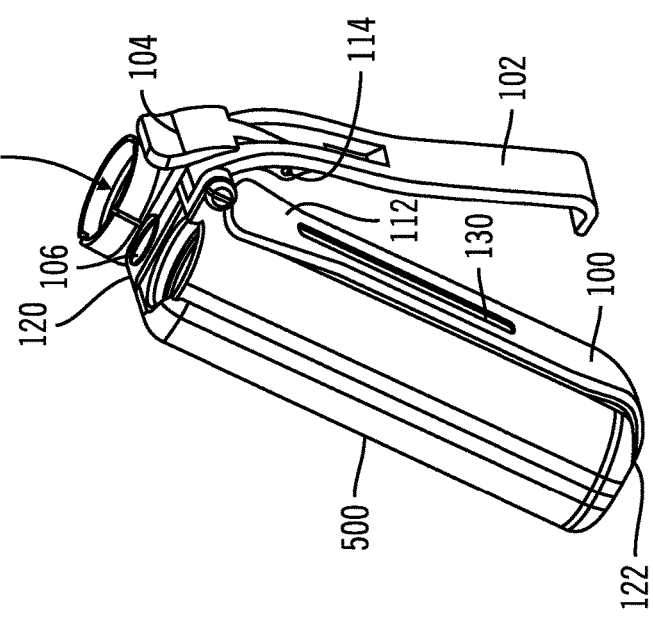

BELT CLIP

RELATED APPLICATIONS

This application is a continuation application of U.S. patent application Ser. No. 14/636,072 filed Mar. 2, 2015, which is herein incorporated by reference.

FIELD OF THE INVENTION

This invention relates to portable medical infusion systems.

BACKGROUND OF THE INVENTION

Diabetes is a disease in which the body does not produce or properly use insulin. Approximately 13 million people in the United States have been diagnosed with some form of diabetes. Type 1 diabetes results from the body's failure to produce insulin. Type 2 diabetes results from insulin resistance in which the body fails to properly use insulin. To effectively manage the disease, diabetics must closely monitor and manage their blood glucose levels through exercise, diet and medication. In particular, both Type 1 and some Type 2 diabetics rely on insulin delivery to control their diabetes. Traditionally, insulin has been injected with a syringe multiple times during the day, usually self-administered by the diabetic. In recent years, use of continuous subcutaneous insulin infusion therapy has been increasing. This therapy delivers insulin to diabetics using devices worn on a belt, in a pocket, or the like, with the insulin delivered from a reservoir via a catheter with a percutaneous needle or cannula placed in the subcutaneous tissue.

External infusion devices allow Type 1 and Type 2 diabetics to better manage and control their diabetes. The external infusion device is intended to be used continuously and delivers insulin twenty-four hours a day according to a programmed plan unique to each pump wearer. A small amount of insulin, or a basal rate, is given continually. This insulin keeps the user's blood glucose levels in the desired range between meals and overnight. When food is eaten, the user programs the external infusion device to deliver a bolus of insulin matched to the amount of food that will be consumed. The user determines how much insulin will be given based on factors including insulin sensitivity, insulin duration, insulin-on-board, and the like. In many instances, external infusion devices include a processor that assists the user in making therapy decisions based on information provided by the user including blood glucose levels, carbohydrate intake, and/or information from the external infusion device. Exemplary devices are described in U.S. Pat. No. 6,554,798 issued on Apr. 29, 2003 to Mann et al., and entitled "External Infusion Device with Remote Programming, Bolus Estimator and/or Vibration Alarm Capabilities," which is specifically incorporated by reference herein.

A belt clip can enable easy access to the external infusion device while allowing the infusion device to be securely held in position while being discrete and inconspicuous. Movement of the infusion set from accidental displacement of the infusion device or tubing can adversely affect the delivery and efficacy of the infusion therapy. Additionally, belt clip breakage can adversely affect overall user satisfaction because the infusion device must be carried in a pocket or a different location until a replacement belt clip is obtained. Accordingly, it can be beneficial to have a belt clip that minimizes the likelihood of breaking the belt clip while protecting the infusion device and minimizing the likelihood of displacing or shifting the infusion set.

SUMMARY OF THE DISCLOSURE

In one embodiment a belt clip assembly is disclosed. The belt clip assembly includes a device retainer having a first retainer defined to retain a clip pin. The belt clip assembly further includes a clip coupled to the device retainer via the clip pin and the clip includes a detent and the clip is further defined to retain a tab pin. A tab is coupled to the clip via the tab pin and the tab is rotatable about the tab pin. The device retainer is initially rotatable about the clip pin independent of rotation of the tab about the tab pin. Additionally, rotation of the device retainer about the clip pin results in a finite displacement of the device retainer.

In another embodiment a portable infusion system is disclosed. The portable infusion system includes an infusion device having a reservoir removably coupled to tubing and the tubing is further removably coupled to an infusion set having a cannula. The portable infusion system further includes a belt clip assembly that includes a device retainer defined to secure a clip pin. The belt clip assembly further includes a clip that is coupled to the device retainer via the clip pin. The clip includes a tab coupled to the clip via a tab pin and the tab is rotatable about the tab pin. The infusion device is secured to the belt clip assembly via the first retainer and the device retainer is initially rotatable about the clip pin independent of rotation of the tab about the tab pin, such that rotation of the device retainer about the clip pin results in a finite displacement of the tubing.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIGS. 3A and 3B illustrate an exemplary view of the belt clip assembly and an associated cross-section E-E, in accordance with embodiments of the present invention.

FIGS. 5A-5C are exemplary illustrations of a portable infusion device within a belt clip assembly rotating about an axis defined by the clip pin, in accordance with embodiments of the present invention.

DETAILED DESCRIPTION

Figure 1:
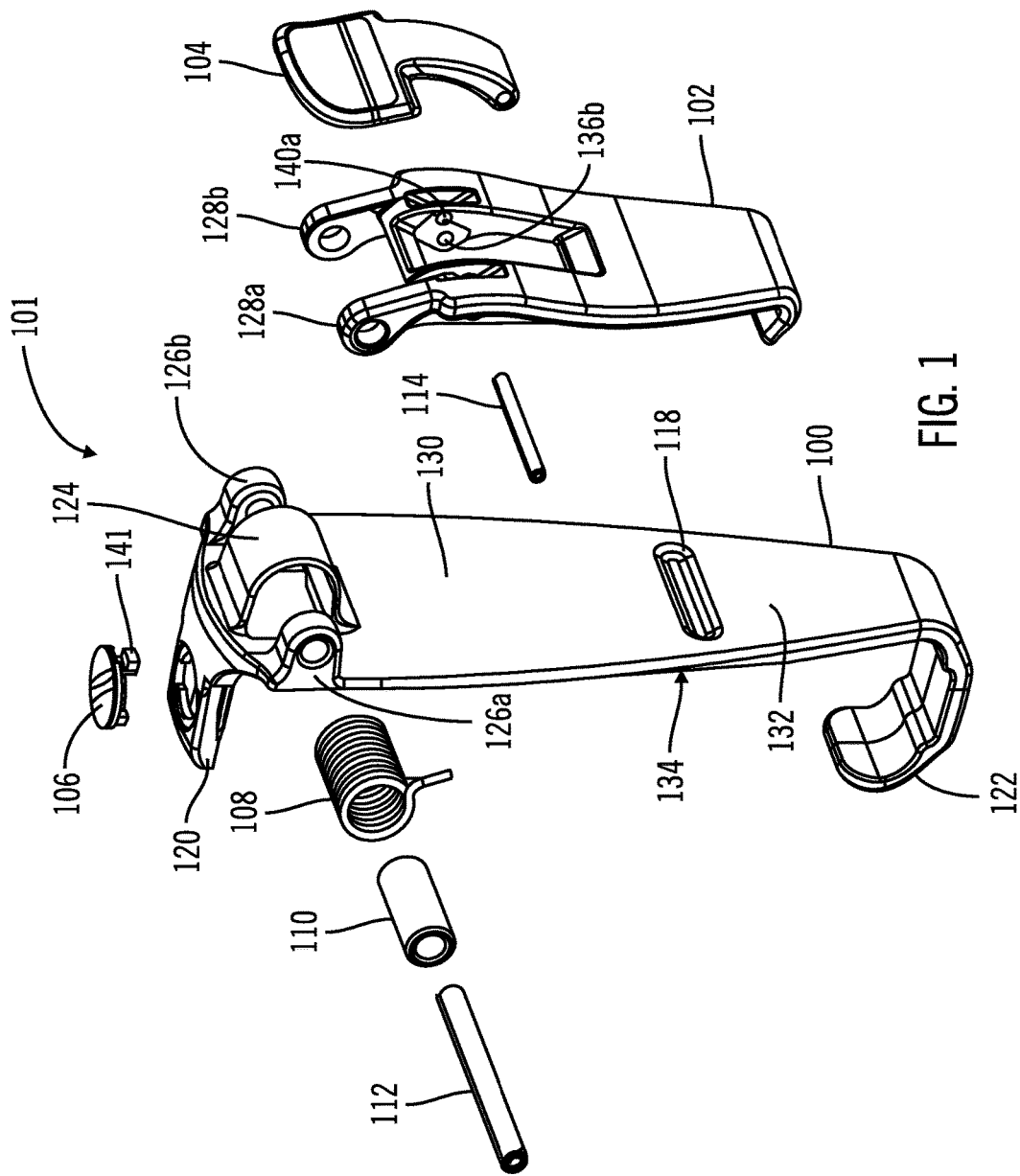
FIG. 1 is an exemplary exploded illustration of components that make up a belt clip assembly, in accordance with embodiments of the present invention.

As shown in the drawings for purposes of illustration, the invention is embodied as a belt clip assembly. The geometry of the belt clip assembly can be configured to accommodate a variety of different portable devices such as, but not limited to portable external infusion systems. A belt clip designed to hold an external infusion device has various design challenges that generally are not present regarding many other portable electronic devices. For example, with some embodiments the infusion device is directly connected via tubing to an infusion set having a cannula inserted into the user. Thus, while belt clips for portable electronic devices can allow the electronic device to spin freely, if applied to a portable infusion device the free rotation could lead to tangled or displaced tubing and displacement of the infusion set.

FIG. 1 is an exemplary exploded illustration of components that make up a belt clip assembly 101, in accordance with embodiments of the present invention. The belt clip assembly 101 includes a device retainer 100. The device retainer 100 includes features such as a first retainer 120 and a second retainer 122. Further associated with the first retainer 120 is a device lock 106. In some embodiments the device lock 106 secures a device within the device retainer 100. In some embodiments that utilize a device lock 106 the second retainer 122 is optional. In other embodiments, the device is secured within the device retainer 120 between the first retainer 120 and the second retainer 122. Additionally, the location and orientation of the first retainer 120 and second retainer 122 as shown in the Figures should not be construed as limiting. In various other embodiments the first retainer and optional second retainer can be positioned in various locations in order to properly retain a device and provide access to any screen or user interface associated with the device. In particular embodiments the device is a medical device, such as, but not limited to a portable infusion device.

Between the top retainer 120 and the second retainer 122 is a device retainer web 130 having a back face 132 and a front face 134. Formed on the back face 132 is a clip hook detent 118 along with a spring housing 124 and retainer journals 126a and 126b. Another component of the belt clip assembly 101 is a clip 102. The clip 102 includes clip journals 128a and 128b along with tab journals 136a (not shown) and 136b. Clip journals 128a and 128b are defined to fit between retainer journals 126a and 126b and the spring housing 124, respectively. Further included on the clip 102 is a clip hook 116 along with detents 140a (not shown) and 140b. When fully assembled, the clip hook 116 is defined to rest with the clip hook detent 118. As shown in FIG. 1, the belt clip assembly 101 further includes a clip pin 112, a clip barrel 110 and a clip spring 108. In some embodiments the clip barrel 110 is optional because the clip pin 112 and clip spring 108 can be sized as to make the clip barrel 110 superfluous. A tab pin 114 secures a tab 104 to the clip 102 through tab journals 136a and 136b.

Figure 2A:
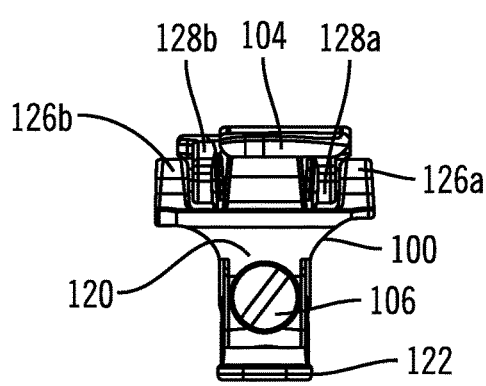
FIGS. 2A-2D are various views of the belt clip assembly in accordance with embodiments of the present invention.

FIGS. 2A-2D are various views of the belt clip assembly 101 in accordance with embodiments of the present invention. FIG. 2A is a top view of the belt clip assembly 101. Device lock 106 is installed in the first retainer 120 of the device retainer 100. In some embodiments the device lock 106 includes a feature 141 (FIG. 1) that enables coupling of a device to the belt clip assembly. In other embodiments the device lock 106 can include multiple features to couple the device to the belt clip assembly. In still other embodiments the device lock is eliminated and the second retainer 122 and the first retainer 120 secure a device within the belt clip assembly. FIG. 2A further illustrates the relative position of the retainer journals 126a and 126b, the clip journals 128a and 128b, a tab 104 and the spring housing 124.

Figure 2B:
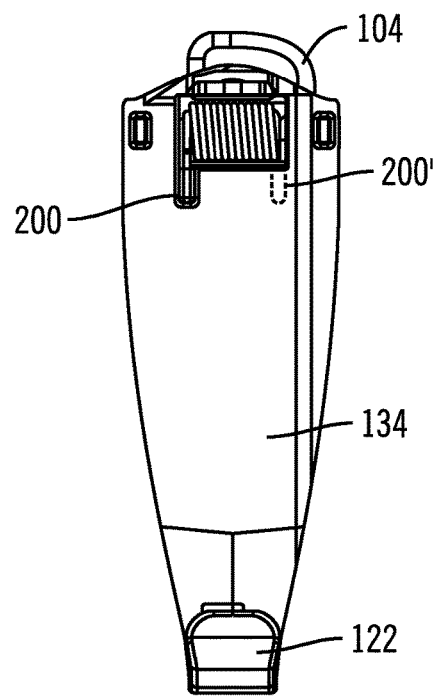

FIG. 2B is a front view of the belt clip assembly 101. In one embodiment the clip spring 108 is a torsion spring having tangential hook ends as shown in FIG. 2B. In other embodiments, the spring clip 108 can be a torsion spring having straight legs or even looped ends. The device retainer 100 can include a spring retainer 200 defined to accept a leg of the clip spring 108. While FIG. 2B includes a single spring retainer 200, other embodiments include an optional second spring retainer 200' to create symmetry in order to expedite mass production of the belt clip assembly 101. In other embodiments using different spring designs, the spring retainer 200 and optional second spring retainer 200' can be defined to retain the appropriate type of spring leg.

Figure 2C:
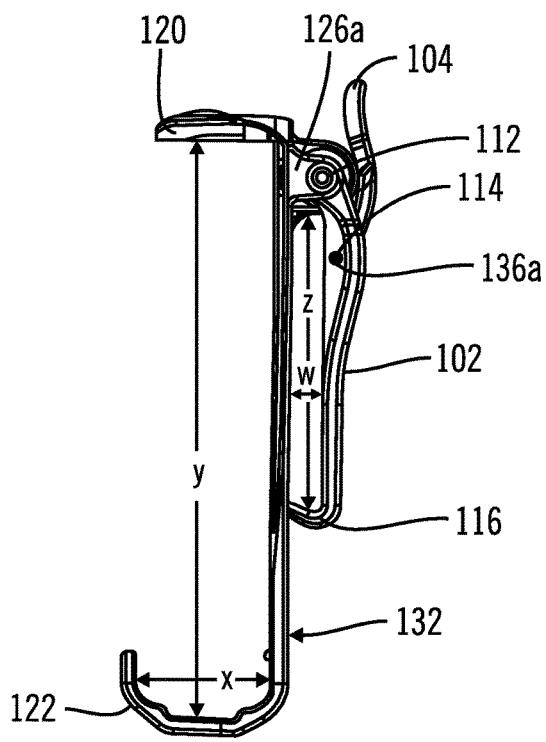

FIG. 2C is a view of the right side of the belt clip assembly 101 and illustrates various exemplary dimensions of the device retained within the belt clip assembly 101. For example, a dimension Y is defined between the first retainer 120 and the second retainer 122. Similarly, a dimension X can be defined as the distance between the second retainer 122 and the front face 134. Additionally, a dimension W is further defined as the distance between the back face 132 and the clip 102 while a dimension Z is defined roughly as the distance between the spring housing 124 and the clip hook 116. In many embodiments the dimension Z is defined to accommodate a variety of belt widths.

Figure 2D:
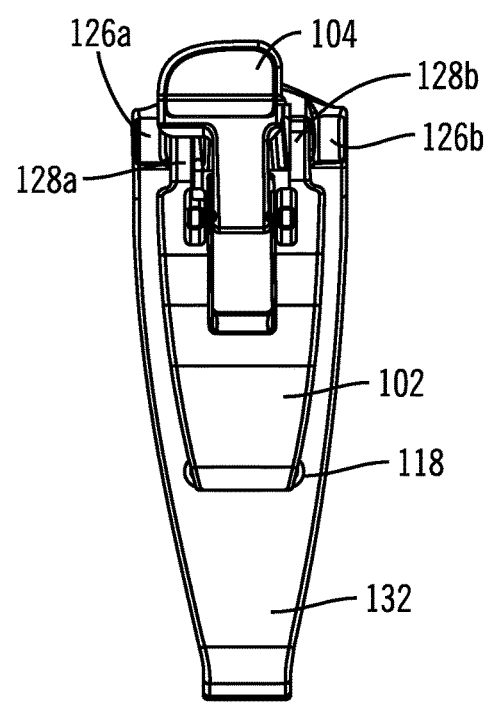

FIG. 2D is a view of the back of the belt clip assembly 101. The tab 104 is shown coupled to the clip 102 using the tab pin 114 (FIGS. 1 and 2C). Similarly, the clip 102 is illustrated coupled to the device retainer 100 using the clip pin 112 (FIGS. 1 and 2C) through the retainer journals 126a and 126b along with clip journals 128a and 128b. The clip hook detent 118 is partially visible on the back face 132 of the device retainer 100.

FIGS. 3A and 3B illustrate an exemplary view of the belt clip assembly 101 and an associated cross-section E-E, in accordance with embodiments of the present invention. FIG. 3A is an exemplary view of the back of the belt clip assembly and further includes the section line E-E to create the view found in FIG. 3B. Accordingly, FIG. 3B is an exemplary illustration of a cross-section of the belt clip assembly. FIG. 3B enables discussion of interactions between the tab 104, the clip 102 and the device retainer 100 relative to moments created about tab pin 114 and clip pin 112. Tab 104 includes a back surface 300 curved to compliment the spring housing 124. As illustrated, back surface 300 is actually in contact with the spring housing 124 so when force F1 is applied to tab 104, the clip 102 and attached tab 104 will rotate about clip pin 112 while the rotation is resisted by the clip spring. The rotation about the clip pin 112 results in the clip hook 116 being displaced in direction D1. However, if a force F2 is applied to the back surface 300 of tab 104, the tab 104 would rotate about tab pin 114. Detents 140a and 140b, formed on the clip 102 help prevent the tab 104 from falling in direction D2. However, detents 140a and 140b (FIG. 1) are not defined to totally prevent rotation of the tab 104 about tab pin 114. As will be discussed later, in some instances the tab 104 is specifically intended to be displaced beyond detents 140a and 140b.

Figure 4A:
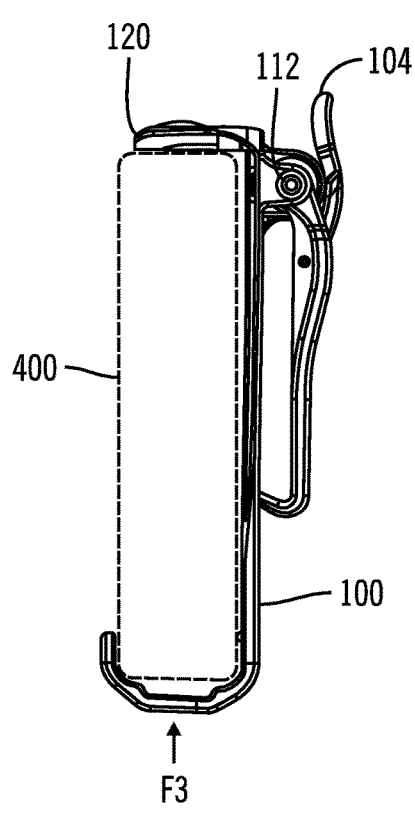
FIGS. 4A and 4B are exemplary illustrations showing rotation of the device retainer about an axis defined by the clip pin, in accordance with embodiments of the present invention.
Figure 4B:
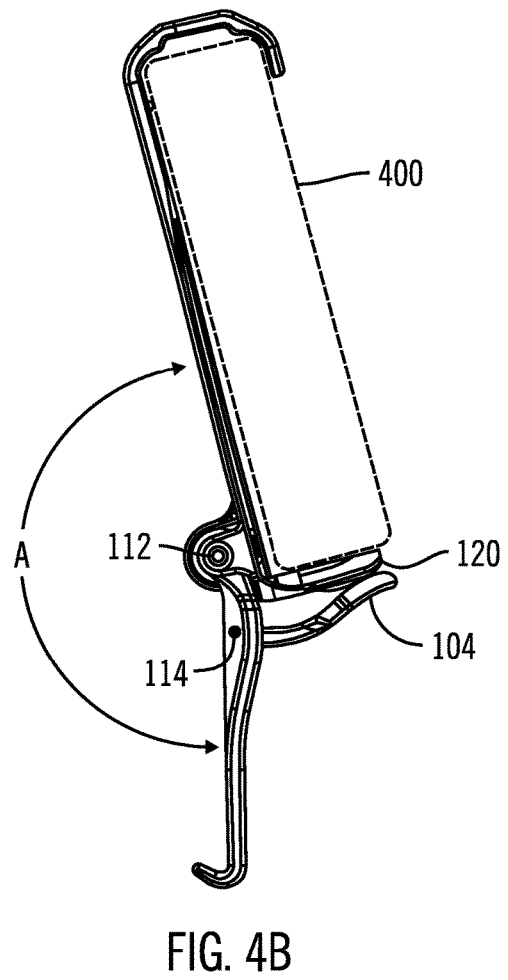

FIGS. 4A and 4B are exemplary illustrations showing rotation of the device retainer 100 about an axis defined by the clip pin 112, in accordance with embodiments of the present invention. FIG. 4A is a side profile view of the belt clip assembly 101 and further includes an outline of device 400 within the device retainer 100. FIG. 4A shows the belt clip assembly 101 during normal use as if the belt clip assembly 101 was attached to a belt. FIG. 4B illustrates rotational displacement of the device retainer 100 about the clip pin 112 if the belt clip assembly were attached to a belt and a force F3 was applied to the device retainer 100. FIG. 4B can further be understood as an exemplary illustration of displacement of the device retainer 100 if a user sits down and the device retainer 100 is caught on an arm of the chair. In some embodiments the displacement of the device retainer 100 from the position shown in FIG. 4A to the position in FIG. 4B is measured by angle A in FIG. 4B. In particular embodiments angle A is more than 180° while in still further embodiments angle A is less than 180°. In still further embodiments angle A is between 160° and 180°. Material selection can also influence angle A as more flexible materials can enable angle A to be larger. In some embodiments copolyester polymer materials such as, but not limited to Eastman TRITAN and the like are used to make the device retainer 100, the clip 102 and the tab 104. In one embodiment TRITAN MX711 is used for the polymer components of the belt clip assembly. In other embodiments different materials can be used for the various parts of the belt clip assembly.

In some embodiments, initial displacement of the device retainer 100 results in the device retainer 100 rotating about the clip pin 112 independent of movement of the clip 104. However, as the device retainer 100 continues to be displaced toward the position shown in FIG. 4B, portions of the first retainer 120 and portions of the device lock 106 come into contact with the tab 104. In these instances continued displacement of the device retainer 100 results in the tab 104 being rotationally displaced about the tab pin 114. During this rotational displacement the tab 104 can be moved beyond detents 140a and 140b to accommodate the displacement of the device retainer 100. After the tab 104 is displaced beyond detents 140a and 140b, the tab 104 can be reset to the position shown in FIG. 4A.

In other embodiments, a second torsion spring is used in association with the tab pin 114 to keep the tab 104 positioned as shown in FIG. 4A. This would still permit the tab 104 to rotate about the tab pin 114 but would automatically reset the tab 104 after displacement. The displacement of the device retainer 100 allows for secure movement of the device 400 should the device 400 within the belt clip assembly 101 encounter an obstruction imparting a vertical load on the clip assembly 101. The accommodation of vertical displacement permits secure movement of the device 400 while minimizing the likelihood of disrupting placement of the cannula via movement of associated tubing. If the device retainer 100 was unable to rotate about the clip pin 112 it is possible that the belt clip could break or result in enough shifting of the attached tubing to move the cannula.

FIGS. 5A-5C are exemplary illustrations of a portable infusion device 500 within a belt clip assembly 101 rotating about an axis defined by clip pin 122, in accordance with embodiments of the present invention. The portable infusion device 500 is held within the device retainer 100 between the first retainer 120 that is joined to the second retainer 122 by the device retainer web 130. As shown in FIG. 5B, the infusion device 500 includes a mating face 504 to accommodate the first retainer 120. In the embodiment shown in FIG. 5B the interface between the mating face 504 and the first retainer 120 can help prevent the infusion device from being dislodged from the device retainer 100. The optional device lock 106 further assists in preventing the infusion device 500 from being dislodged from the device retainer 100. In embodiments that include the device lock 106 the mating face 504 can further include features that detachably couples the infusion device 500 to the belt clip assembly 101 via the device lock 106.

Cavity 502 of the infusion device 500 is defined to receive a reservoir and tubing that can be removably coupled to an infusion set. The infusion device is defined to pump fluid from the reservoir through the tubing into a user via the infusion set. In some embodiments the infusion set includes a cannula that is inserted into subcutaneous tissue of the user. In other embodiments the infusion set can be placed intravenously. The specific example provided should not be construed as limiting as other embodiments can place the infusion set in different locations. As shown in FIGS. 5A-5C, rotation of the infusion device 500 about the clip pin 112 from the position in FIG. 5A to the position in FIG. 5C results in the cavity 502 being displaced a finite and minimal distance. It is advantageous to minimize the distance traversed by the cavity 502 to minimize the likelihood of moving or shifting tubing from the reservoir that is connected to the infusion set.

Figures 6A, 6B, 6C:
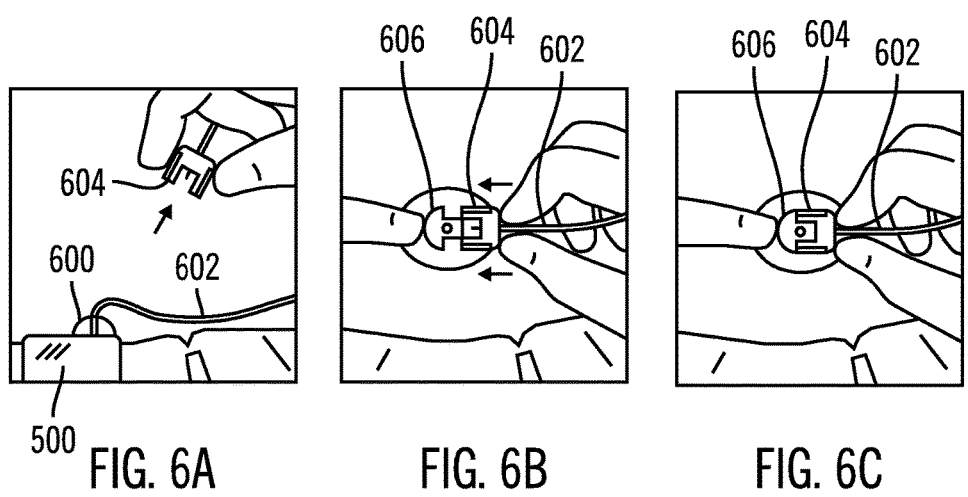
FIGS. 6A-6C are exemplary illustrations of an infusion device with a reservoir connected to tubing that is further connected to an infusion set, in accordance with embodiments of the present invention.

FIGS. 6A and 6C are exemplary illustrations of an infusion device 500 with a reservoir 600 connected to tubing 602 that is further connected to an infusion set 606, in accordance with embodiments of the present invention. In some embodiments, the reservoir 600 shown in FIG. 6A is installed in cavity 502 in FIGS. 5A-5C. One end of the tubing 602 can be permanently or detachably connected to the reservoir 600 while the second end can be terminate with connector 604 in FIG. 6B. The connector 604 can further be removably coupled with an infusion set 606 that includes a cannula to administer fluid transmitted through the tubing into a user. FIG. 6C is an exemplary illustration of the connector 604 being connected with an infusion set 606. Once connected as shown in FIG. 6C, force applied to infusion device 500 can be transmitted via the tubing 602 to the infusion set 606. While the tubing 602 can include slack to minimize potential movement of the infusion set 606 the belt clip assembly can further reduce the likelihood of excessive force being applied to the infusion set 606 if the infusion device 500 is displaced.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A belt clip assembly, comprising:
 a device retainer having a first retainer, the device retainer further defined to retain a clip pin;
 a clip coupled to the device retainer via the clip pin and being rotatable about the clip pin, the clip further defined to retain a tab pin; and
 a tab coupled to the clip via the tab pin, the tab being rotatable about the tab pin,
 wherein the device retainer is initially rotatable about the clip pin independent of rotation of the clip about the clip pin, such that rotation of the device retainer about the clip pin results in a finite displacement of the device retainer.

2. The belt clip assembly of claim 1, further comprising a device lock defined on the first retainer.

3. The belt clip assembly of claim 1, wherein the device retainer further has a second retainer.

4. The belt clip assembly of claim 3, further comprising a device lock defined on the first retainer.

5. The belt clip assembly of claim 1, wherein continued rotation of the device retainer about the clip pin results in rotation of the tab about the tab pin.

6. The belt clip assembly of claim 5, wherein the clip further includes at least one detent defined to resist rotation of the tab about the tab pin.

7. The belt clip assembly of claim 6, wherein the continued rotation of the device retainer about the clip pin results in rotation of the tab about the tab pin beyond the at least one detent.

8. A portable infusion system, comprising:
   an infusion device including a reservoir removably coupled to tubing, the tubing further being removably coupled to an infusion set having a cannula; and
   a belt clip assembly including
      a device retainer having a first retainer, the device retainer further defined to retain a clip pin,
      a clip coupled to the device retainer via the clip pin and being rotatable about the clip pin, the clip further defined to retain a tab pin, and
      a tab coupled to the clip via the tab pin, the tab being rotatable about the tab pin,
      wherein the infusion device is secured to the belt clip assembly via the first retainer and the device retainer is initially rotatable about the clip pin independent of rotation of the clip about the clip pin, such that rotation of the device retainer about the clip pin results in a finite displacement of the tubing.

9. The portable infusion system of claim 8, further comprising a device lock defined on the first retainer, wherein the infusion device is secured to the belt clip assembly via the first retainer and the device lock.

10. The portable infusion system of claim 8, wherein the device retainer further has a second retainer, and wherein the infusion device is secured to the belt clip assembly via the first retainer and the second retainer.

11. The portable infusion system of claim 10, further comprising a device lock defined on the first retainer, wherein the infusion device is secured to the belt clip assembly via the first retainer, the second retainer, and the device lock.

12. The portable infusion system of claim 8, wherein continued rotation of the device retainer about the clip pin results in rotation of the tab about the tab pin.

13. The portable infusion system of claim 12, wherein the clip further includes at least one detent defined to resist rotation of the tab about the tab pin.

14. The portable infusion system of claim 13, wherein the continued rotation of the device retainer about the clip pin results in rotation of the tab about the tab pin beyond the at least one detent.

* * * * *